US00PP19292P2

(12) United States Plant Patent
Verwer

(10) Patent No.: US PP19,292 P2
(45) Date of Patent: Oct. 7, 2008

(54) ***DAHLIA* PLANT NAMED 'VDTG43'**

(50) Latin Name: *Dahlia hybrida*
Varietal Denomination: VDTG43

(75) Inventor: Aad W. M. Verwer, DL Lisse (NL)

(73) Assignee: Verwer Dahlias B.V., Lisse (NL)

( * ) Notice: Subject to any disclaimer, the term of this patent is extended or adjusted under 35 U.S.C. 154(b) by 0 days.

(21) Appl. No.: 11/890,471

(22) Filed: Aug. 6, 2007

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent L Bell
(74) *Attorney, Agent, or Firm*—C. A. Whealy

(57) ABSTRACT

A new and distinct cultivar of *Dahlia* plant named 'VDTG43', characterized by its compact, upright, somewhat outwardly spreading and mounded plant habit; freely branching growth habit; dark-colored foliage; freely flowering habit; daisy-type inflorescence form; inflorescences with light and dark purple-colored ray florets; and good postproduction longevity and garden performance.

1 Drawing Sheet

Botanical designation: *Dahlia hybrida.*
Cultivar denomination: 'VDTG43'.

BACKGROUND OF THE INVENTION

The present invention relates to a new and distinct cultivar of *Dahlia* plant, botanically known as *Dahlia hybrida,* and hereinafter referred to by the name 'VDTG43'.

The new *Dahlia* is a product of a planned breeding program conducted by the Inventor in Lisse, The Netherlands. The objective of the breeding program is to create new compact container-type *Dahlia* cultivars that have a freely branching growth habit, early and freely flowering habit, daisy inflorescence form, attractive ray floret coloration, and good postproduction longevity and garden performance.

The new *Dahlia* originated from an open-pollination in Lisse, The Netherlands during the summer of 2003 of a proprietary seedling selection of *Dahlia hybrida* identified as code R, not patented, as the female, or seed, parent with an unidentified selection of *Dahlia hybrida,* as the male, or pollen, parent. The new *Dahlia* was discovered and selected by the Inventor as a single flowering plant within the progeny of the stated open-pollination in a controlled environment in Lisse, The Netherlands during the summer of 2004.

Asexual reproduction of the new *Dahlia* by cuttings since the spring of 2005 in a controlled environment in Lisse, The Netherlands, has shown that the unique features of this new *Dahlia* are stable and reproduced true to type in successive generations.

SUMMARY OF THE INVENTION

The cultivar VDTG43 has not been observed under all possible environmental conditions. The phenotype may vary somewhat with variations in environment such as temperature and light intensity, without, however, any variance in genotype.

The following traits have been repeatedly observed and are determined to be the unique characteristics of 'VDTG43'. These characteristics in combination distinguish 'VDTG43' as a new and distinct cultivar of *Dahlia:*

1. Compact, upright, somewhat outwardly spreading and mounded plant habit.
2. Freely branching growth habit.
3. Dark-colored foliage.
4. Freely flowering habit.
5. Daisy-type inflorescence form.
6. Inflorescences with light and dark purple-colored ray florets.
7. Good postproduction longevity and garden performance.

Plants of the new *Dahlia* differ from plants of the female parent selection in the following characteristics:

1. Plants of the new *Dahlia* are more freely branching than plants of the female parent selection.
2. Plants of the new *Dahlia* and the female parent selection differ in ray floret coloration as plants of the female parent selection have red-colored ray florets.

Plants of the new *Dahlia* can be compared to plants of the *Dahlia* cultivar Scura, not patented. In side-by-side comparisons conducted in Lisse, The Netherlands, plants of the new *Dahlia* differed from plants of the cultivar Scura in the following characteristics:

1. Plants of the new *Dahlia* were more compact than plants of the cultivar Scura.
2. Plants of the new *Dahlia* had darker colored foliage than plants of the cultivar Scura.
3. Plants of the new *Dahlia* had larger inflorescences than plants of the cultivar Scura.
4. Plants of the new *Dahlia* and the cultivar Scura differed in ray floret color as plants of the cultivar Scura had orange red-colored ray florets.

BRIEF DESCRIPTION OF THE PHOTOGRAPH

The accompanying photograph illustrates the overall appearance of the new *Dahlia.* The photograph shows the colors as true as it is reasonably possible to obtain in colored reproductions of this type. Colors in the photograph may differ slightly from the color values cited in the detailed botanical description which accurately describe the colors of the new *Dahlia*. The photograph comprises a side perspective view of a typical flowering plant of 'VDTG43' grown in a container.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Lisse, The Netherlands during the summer and autumn in an outdoor nursery and under conditions and practices which approximate those generally used in commercial *Dahlia* production. During the production of the plants, day temperatures ranged from 15° C. to 30° C. and night temperatures ranged from 10° C. to 20° C. Plants were pinched one time about three to four weeks after planting. Measurements and numerical values represent averages for typical flowering plants. Plants were about three to four months old when the photographs and description were taken.

Botanical classification: *Dahlia hybrida* cultivar VDTG43.

Parentage:

*Female, or seed, parent.*—Proprietary seedling selection of *Dahlia hybrida* identified as code R, not patented.

*Male, or pollen, parent.*—Unidentified selection of *Dahlia hybrida,* not patented.

Propagation:

*Type.*—By cuttings.

*Time to initiate roots, summer.*—About five days at temperatures of about 20° C. to 22° C.

*Time to initiate roots, winter.*—About seven days at temperatures of about 20° C. to 22° C.

*Time to produce a rooted young plant, summer.*—About 20 days at temperatures of about 20° C. to 22° C.

*Time to produce a rooted young plant, winter.*—About 22 days at temperatures of about 20° C. to 22° C.

*Root description.*—Medium in thickness, fleshy; 157D in color. If tubers develop, they are corky in texture and 199B in color.

*Rooting habit.*—Moderate branching; moderately dense.

Plant description:

*Plant form/growth habit.*—Compact, upright to somewhat outwardly spreading; mounded plant form. Freely basal branching with about five primary lateral branches; dense and bushy plant habit. Inflorescences held above the foliage on strong peduncles. Vigorous growth habit.

*Plant height.*—About 22 cm.

*Plant diameter or spread.*—About 15 cm.

*Lateral branches.*—Length: About 18 cm. Diameter: About 1.6 cm. Internode length: About 1.5 cm to 7 cm. Aspect: Erect to about 15° from vertical. Strength: Strong. Texture: Smooth, glabrous. Color: Towards the base, 13A; towards the apex, 178A.

Foliage description:

*Arrangement.*—Leaves opposite; leaves may be single or compound with three or five leaflets.

*Shape.*—Ovate.

*Apex.*—Acuminate.

*Base.*—Attenuate.

*Margin.*—Serrate and divided; sinuses divergent.

*Length.*—Single leaves: About 5 cm. Compound leaves with three leaflets: About 11 cm. Compound leaves with five leaflets: About 15 cm.

*Width.*—Single leaves: About 2.4 cm. Compound leaves with three leaflets: About 4.5 cm. Compound leaves with five leaflets: About 7 cm.

*Venation pattern.*—Pinnate.

*Texture, upper and lower surfaces.*—Smooth, glabrous.

*Color.*—Developing foliage, upper surface: 139A. Developing foliage, lower surface: Darker than 191A. Fully expanded foliage, upper surface: 139A; venation, 185C. Fully expanded foliage, lower surface: Close to 191A; venation, 148A.

*Petiole length.*—About 1 cm to 4 cm.

*Petiole diameter.*—About 2 mm.

*Petiole texture, upper and lower surfaces.*—Smooth, glabrous.

*Petiole color, upper surface.*—187B.

*Petiole color, lower surface.*—148B.

Inflorescence description:

*Appearance.*—Rotate single inflorescence form with ray and disc florets. Inflorescences positioned above the foliage on strong peduncles. Inflorescences face upright to slightly outwardly. Freely flowering habit; about 25 inflorescences develop per plant. Inflorescences persistent. Inflorescences not fragrant.

*Time to flower.*—Plants flower continuously during the summer and autumn in The Netherlands.

*Post-production longevity.*—Inflorescences maintain good substance for about ten days on the plant and for about four to five days as a cut flower.

*Inflorescence bud.*—Height: About 1.2 cm. Diameter: About 1.1 cm. Shape: Oblate to globular. Color: Towards the base, 138A; towards the apex, 177B.

*Inflorescence size.*—Diameter: About 5.5 cm. Depth (height): About 1.6 cm. Disc diameter: About 1.4 cm. Receptacle height: About 6 mm. Receptacle diameter: About 1.2 cm.

*Ray florets.*—Length: About 2.3 cm. Width: About 1.1 cm. Shape: Ovate. Apex: Obtuse. Base: Attenuate. Aspect: Initially upright to roughly perpendicular to the peduncle. Texture, upper and lower surfaces: Smooth, glabrous; satiny. Number of ray florets per inflorescence: About twelve arranged in a single whorl. Color: When opening and fully opened, upper surface: Towards the base, 59B; towards the apex, 75B; along the veins, 59B. When opening and fully opened, lower surface: Towards the base, 61A; towards the apex, 73A.

*Disc florets.*—Shape: Tubular; apex dentate. Length: About 8 mm. Diameter: Less than 1 mm. Number of disc florets per inflorescence: About 130. Color: Immature: Towards the apex, 187A; mid-section, 171A; towards the base, 154C. Mature: Towards the apex, 20A; mid-section, 171A; towards the base, 154C.

*Phyllaries.*—Quantity per inflorescence: About five arranged in a single whorl. Length: About 8 mm. Width: About 6 mm. Shape: Ovate. Apex: Acute. Base: Attenuate. Margin: Entire. Texture, upper and lower surfaces: Smooth, glabrous. Color, upper surface: 200A. Color, lower surface: 200B.

*Peduncles.*—Length: Terminal peduncle: About 7 cm. Fourth peduncle: About 5 cm. Seventh peduncle: About 3 cm. Diameter: About 7 mm. Strength: Strong. Aspect: Erect to about 20° from vertical. Texture: Smooth, glabrous. Color: 187C.

*Reproductive organs.*—Androecium: Quantity per disc floret: Five. Filament length: About 4 mm. Filament color: 2B. Anther shape: Lanceolate. Anther length: About 1.9 mm. Anther color: 17A. Pollen amount: Abundant. Pollen color: 21A. Gynoecium: Quantity per ray or disc floret: One. Pistil length: About 2 mm. Stigma shape: Lanceolate. Stigma color: 13C. Style length: About 1.7 mm. Style color: Close to 13A. Ovary color: 9B. Seeds: Length: About 4 mm. Diameter: About 1.3 mm. Color: 200D. Fruits: Length: About 1.8 cm. Diameter: About 1.8 cm. Color: 187A.

Disease/pest resistance: Plants of the new *Dahlia* have not been shown to be resistant to pathogens and pests common to *Dahlia*.

Garden performance: Plants of the new *Dahlia* have exhibited good tolerance to rain and wind and have been observed to tolerate temperatures from about 0° C. to about 45° C.

It is claimed:

1. A new and distinct *Dahlia* plant named 'VDTG43' as illustrated and described.

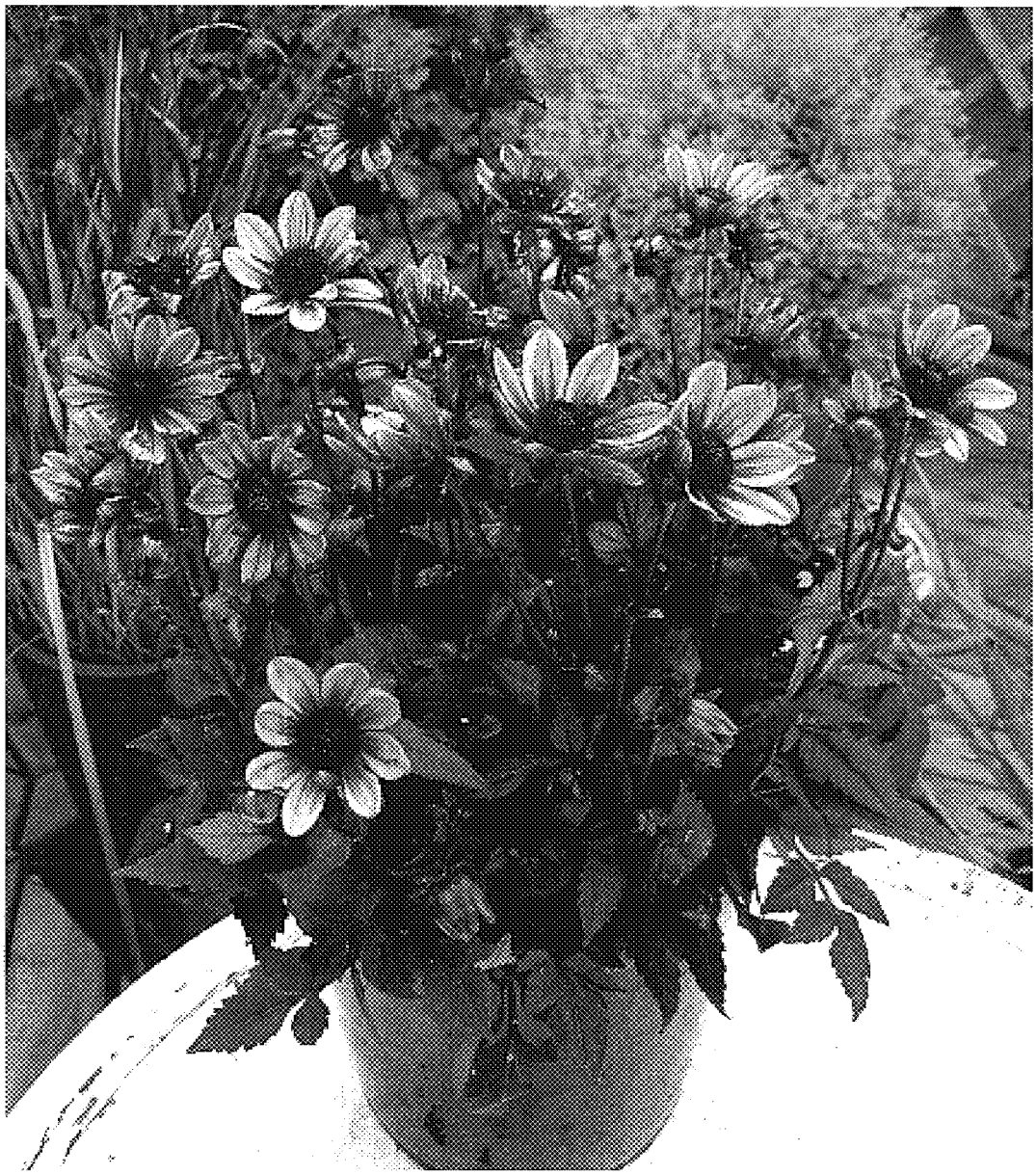

* * * * *